US011890594B2

(12) United States Patent
Hodges et al.

(10) Patent No.: US 11,890,594 B2
(45) Date of Patent: Feb. 6, 2024

(54) CHEMICAL HOMOGENEITY AND CATALYTIC PERFORMANCE OF MIXED-METAL OXIDE CATALYSTS

(71) Applicant: UOP LLC, Des Plaines, IL (US)

(72) Inventors: James M. Hodges, Boalsburg, PA (US); Joel T. Walenga, Lake Zurich, IL (US); Scott Lyle Nauert, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/722,204

(22) Filed: Apr. 15, 2022

(65) Prior Publication Data
US 2023/0211319 A1 Jul. 6, 2023

Related U.S. Application Data

(60) Provisional application No. 63/295,277, filed on Dec. 30, 2021.

(51) Int. Cl.
*B01J 23/00* (2006.01)
*B01J 23/28* (2006.01)
*B01J 37/00* (2006.01)
*B01J 37/04* (2006.01)
*B01J 37/08* (2006.01)
*C07C 5/48* (2006.01)

(52) U.S. Cl.
CPC ............. *B01J 23/28* (2013.01); *B01J 23/002* (2013.01); *B01J 37/0036* (2013.01); *B01J 37/04* (2013.01); *B01J 37/082* (2013.01); *C07C 5/48* (2013.01); *C07C 2523/20* (2013.01); *C07C 2523/22* (2013.01); *C07C 2523/28* (2013.01); *C07C 2523/32* (2013.01)

(58) Field of Classification Search
CPC ....... B01J 23/002; B01J 23/28; B01J 37/0036
See application file for complete search history.

(56) References Cited

U.S. PATENT DOCUMENTS

| 9,073,036 | B2 | 7/2015 | Hagemeyer et al. | |
|---|---|---|---|---|
| 9,254,482 | B2 | 2/2016 | Hagemeyer et al. | |
| 10,065,183 | B2 | 9/2018 | Zander et al. | |
| 10,350,582 | B2 | 7/2019 | Simanzhenkov et al. | |
| 2011/0245571 | A1* | 10/2011 | Kustov ..................... | C07C 5/48 585/658 |
| 2019/0270688 | A1* | 9/2019 | Bos .......................... | B01J 8/067 |
| 2019/0366311 | A1 | 12/2019 | Mestl et al. | |
| 2020/0061583 | A1 | 2/2020 | Mestl et al. | |
| 2020/0139349 | A1 | 5/2020 | Mestl et al. | |
| 2020/0215516 | A1 | 7/2020 | Mestl et al. | |
| 2020/0282383 | A1 | 9/2020 | Simanzhenkov et al. | |

FOREIGN PATENT DOCUMENTS

| WO | WO-2018019761 A1 * | 2/2018 | ............ B01J 23/002 |
|---|---|---|---|
| WO | 2020078980 A1 | 4/2020 | |

* cited by examiner

Primary Examiner — Jun Li
(74) Attorney, Agent, or Firm — Paschall & Associates, LLC; Mark Goldberg

(57) ABSTRACT

A method for preparing a mixed-metal oxide catalyst comprising molybdenum, vanadium, at least one of niobium or tantalum, and at least one of tellurium or antimony and useful for the oxidative dehydrogenation of ethane to ethylene, the method comprising preparing a catalyst precursor, pressing the precursor into a dense pellet using a pressure of greater than about 5,000 psi, and annealing the pellet to form the mixed-metal oxide catalyst.

13 Claims, 3 Drawing Sheets

CHEMICAL HOMOGENEITY AND CATALYTIC PERFORMANCE OF MIXED-METAL OXIDE CATALYSTS

CROSS-REFERENCE TO RELATED APPLICATIONS

This application claims priority from U.S. Provisional Application No. 63/295,277, filed Dec. 30, 2021, which is incorporated herein in its entirety.

FIELD

This disclosure relates to a new method for preparing a mixed-metal oxide catalyst. More particularly this disclosure relates to a novel mixed-metal oxide catalyst comprising molybdenum, vanadium, at least one of niobium or tantalum, and at least one of tellurium or antimony, and its use as an oxidative dehydrogenation catalyst.

BACKGROUND

Ethylene is the most widely produced organic compound in the chemical industry and supports many important processes. Steam cracking is the primary method used to generate ethylene but requires high temperatures (750-900° C.), generates numerous side products including coke that must be periodically removed from reactors, while also having a large carbon footprint. An alternative route to ethylene production is oxidative dehydrogenation of ethane ($C_2$-ODH), which can be accomplished at relatively low temperatures (300-500° C.), delivers high ethylene yields, and exploits a recent surge in ethane-rich shale gas. Still, there are challenges that need to be addressed before this technology can become commercialized, including the development of high-performance catalysts that deliver high ethylene yields and mitigate secondary oxidation of ethane.

MoVNbTe-oxide catalysts (and other related materials) with the M1-type structure have been identified as the best candidates for $C_2$-ODH. The chemical and structural complexity in these systems provides spatially isolated sites that promote C—H bond cleavage while also preventing unwanted secondary oxidations. However, these chemical and structural complexities also present synthetic challenges. Prior art slurry and hydrothermal methods have focused on annealing free powders, which is problematic in that it often produces inhomogeneous materials, and high surface area powders are more susceptible to volatilization of elements during the high temperature treatment.

SUMMARY

A novel method has been developed for preparing a mixed-metal oxide catalyst comprising molybdenum, vanadium, at least one of niobium or tantalum, and at least one of tellurium or antimony and useful for the oxidative dehydrogenation of ethane to ethylene. The method entails preparing a catalyst precursor, pressing the precursor into a dense pellet using a pressure of greater than about 5,000 psi, annealing the pellet to form the mixed-metal oxide catalyst, and optionally grinding the mixed-metal oxide catalyst into a fine powder and repeating steps (b) and (c). The mixed-metal oxide catalyst may have the formula $MoV_xY_yZ_zO_n$, wherein Y=Nb, Ta, or a combination thereof, Z=Te, Sb, or a combination thereof, x=0.1 to 0.4, y=0.05 to 0.3, z=0.05 to 0.3, and n takes a value that satisfies the bond valency of the mixed-metal oxide catalyst; the catalyst further characterized by an x-ray powder diffraction pattern comprising peaks at the diffraction angles 2Θ (°)±0.1 of 6.6, 7.8, 9.0, 22.2, 25.3, 26.2, 27.2, 29.1, 30.4, and 45.1.

Additional features and advantages of the disclosure will be apparent from the description, figures and claims provided herein.

DEFINITIONS

Figure 1:
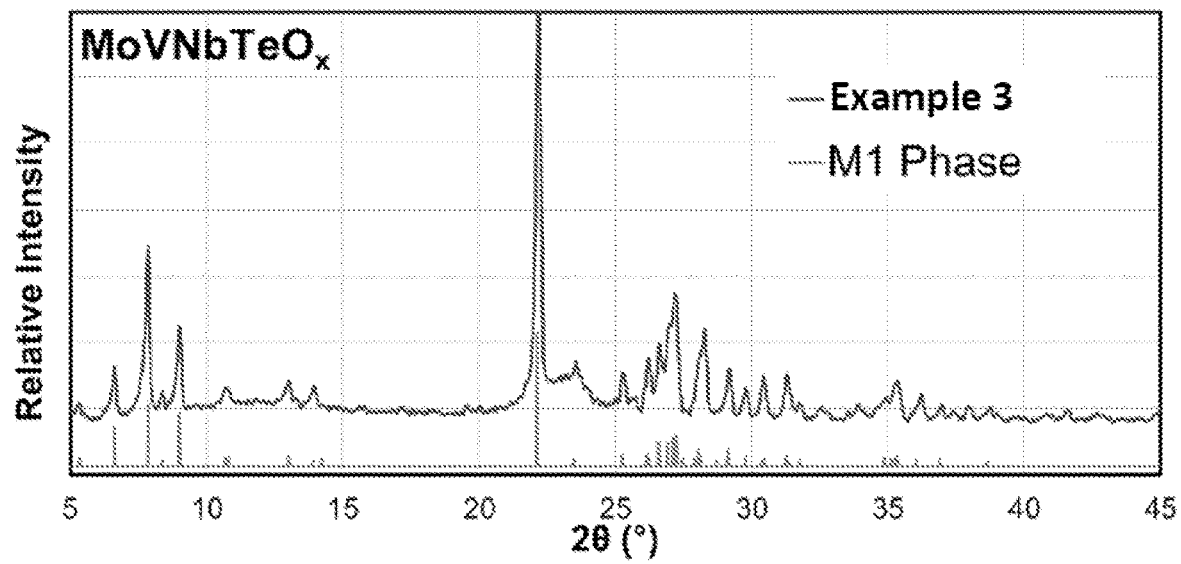
FIG. 1 shows the x-ray powder diffraction pattern of a mixed-metal oxide catalyst prepared by the method described in the Examples compared to the theoretical pattern for an M1-type structure.

The term "selectivity" means the moles of carbon in a product divided by the total moles of carbon in all products excluding the feed.

As used herein, the term "conversion" means $$1 - \frac{\text{(moles of ethane in the effluent)}}{\text{(moles of ethane in the feed)}}$$

DETAILED DESCRIPTION

The present disclosure relates to an innovative approach for improving the elemental homogeneity of M1-type catalysts, which can be used in a variety of systems and is shown to significantly improve catalyst performance. The improved mixed-metal oxide catalysts comprise molybdenum, vanadium, at least one of niobium or tantalum, and at least one of tellurium or antimony and are produced by:

(a) preparing a catalyst precursor comprising molybdenum, vanadium, at least one of niobium or tantalum, and at least one of tellurium or antimony;

(b) pressing the catalyst precursor into a dense pellet using a pressure of greater than about 5,000 psi, preferably greater than about 15,000 psi, or between about 15,000 psi to about 30,000 psi;

(c) annealing the dense pellet at a temperature of from about 525° C. to about 700° C., preferably from about 550° C. to about 625° C., in a non-oxidative environment for a period of from about 0.5 hours to about 24 hours, preferably from about 2 hours to about 12 hours, to form the mixed-metal oxide catalyst; and (d) optionally grinding the mixed-metal oxide catalyst into a fine powder and repeating steps (b) and (c).

In addition, after step (b), the dense pellet may be calcined in an oxidative environment, at a temperature between about 250° C. to about 350° C., before annealing step (c) is carried out The density of the pellet formed in step (b) may range from about 1.5 to about 1.8 g/cm³. The pellet may be formed by any powder compression method such as using hot press, cold press, or extrusion machinery.

The non-oxidative environment of step (c) may be any inert gas such as argon, nitrogen, helium, hydrogen, or a combination thereof, preferably in an environment of less than 0.5 wt % oxygen.

The catalyst precursor may be produced by first preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C., preferably from about 70° C. to about 80° C.; optionally adjusting the pH of the slurry to a value of from about 2.0 to about 4.0, preferably from about 2.0 to about 3.0; and drying the slurry to form the catalyst precursor; wherein the compounds are metallic elements, salts, acids, oxides, hydroxides, oxyhalides or mixtures thereof.

Alternatively, the catalyst precursor may be produced by first preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C., preferably from about 70° C. to about 80° C.; optionally adjusting the pH of the slurry to a value of from about 2.0 to about 4.0, preferably from about 2.0 to about 3.0; and hydrothermally treating the catalyst precursor at a temperature from about 150° C. to about 250° C., preferably from about 170° C. to about 200° C., for about 10 to about 100 hours, preferably from about 24 to about 72 hours; wherein the molybdenum, vanadium, niobium tantalum, tellurium and antimony compounds used to prepare the catalyst precursor may be metallic elements, salts, acids, oxides, hydroxides, oxyhalides or mixtures thereof.

Preferably, the molybdenum, vanadium, niobium tantalum, tellurium and antimony compounds used to prepare the catalyst precursor are oxides.

Specific examples of sources of molybdenum for preparing a catalyst precursor include, but are not limited to, molybdenum trioxide, molybdenum dioxide, molybdic acid, ammonium heptamolybdate, molybdenum chloride, and molybdenum metal.

Specific examples of sources of vanadium include, but are not limited to, a vanadium oxide such as vanadium pentoxide, and soluble vanadium salts such as ammonium metavanadate, vanadyl sulfate, vanadyl chloride and vanadium trichloride.

Specific examples of sources of niobium include, but are not limited to, a niobium oxide such as niobium pentoxide, niobic acid, niobium hydroxide, a soluble niobium salt such as ammonium niobate oxalate hydrate, and niobium pentachloride.

Specific examples of sources of tantalum include, but are not limited to, tantalum pentoxide, tantalum oxalates, and tantalum pentachloride.

Specific examples of sources of tellurium include, but are not limited to, tellurium dioxide, telluric acid, and tellurium metal.

Specific examples of sources of antimony include, but are not limited to, antimony trioxide, and antimony(III) sulfate.

Preferably, the slurry used to prepare the catalyst precursor is produced by preparing a first solution comprising a molybdenum compound, a vanadium compound, and at least one of a tellurium compound and an antimony compound; preparing a second solution at least one of a niobium compound and a tantalum compound, and admixing the first solution and the second solution to form the slurry.

Preferably, the mixed-metal oxide catalyst has the formula $MoV_xY_yZ_zO_n$, wherein Y=Nb, Ta, or a combination thereof, Z=Te, Sb, or a combination thereof, x=0.1 to 0.4, preferably 0.2 to 0.35, y=0.05 to 0.3, preferably 0.1 to 0.15, and z=0.05 to 0.3, preferably 0.15 to 0.25, and n takes a value that satisfies the bond valency of the mixed-metal oxide catalyst, the catalyst further characterized by an x-ray powder diffraction pattern comprising peaks at the diffraction angles 2Θ (°)±0.1 of 6.6, 7.8, 9.0, 22.2, 25.3, 26.2, 27.2, 29.1, 30.4, and 45.1.

The novel mixed-metal oxide catalysts prepared by the methods above may be used for the oxidative dehydrogenation of ethane to ethylene.

The novel crystalline mixed-metal oxide catalyst compositions are characterized by their unique x-ray powder diffraction pattern as shown in Table A.

TABLE A

| 2Θ (°) ± 0.1 |
| --- |
| 6.6 |
| 7.8 |
| 9.0 |
| 22.2 |
| 25.3 |
| 26.2 |
| 27.2 |
| 29.1 |
| 30.4 |
| 45.1 |

Ethane oxidative dehydrogenation using the mixed-metal oxide catalysts may be carried out at a temperature from about 300° C. to about 500° C., preferably from about 350° C. to about 450° C. at a pressure of from about 0.1 to about 20 barg, preferably from about 0.1 to about 10 barg, a space velocity of from about 1000 to about 5000 $cm^3 * g_{cat}^{-1} * h^{-1}$, wherein the molar ratio of ethane to oxygen is about 1.5:1 to 2:1 with sufficient inert diluent to achieve safe operating conditions.

Testing Procedures

Evaluation of catalysts for ethane oxidative dehydrogenation (ODH) is carried out in a fixed bed flow reactor. The molar feed ratios $C_2H_6/O_2/N_2$ may be 1.6/1/5, 1.8/1/5, or 2/1/5. The gas space velocity is 2000±150 $cm^3/g_{cat}/h$ with volumetric flow rate measured at 25° C. and atmospheric pressure. The pressure in the reaction zone is fixed at 15±0.2 psig pressure. 1.0 g of powder catalyst is used for all tests. The reactor consists of an annular quartz reactor with inner diameter 0.1875 inches and outer diameter 0.75 inches, with a thermocouple located in the inner space to measure temperature. Water and oxygenates are condensed in an ice bath downstream of the reaction zone, and gaseous products are analyzed by an online GC system (Agilent 6890). The GC is equipped with TCD and FID detectors. The TCD is used to analyze $O_2$, $N_2$, CO, $CO_2$, and light hydrocarbons, while the FID is used to analyze hydrocarbons.

COMPARATIVE EXAMPLE

A MoVNbTe oxide was synthesized by adding 14.4 g $MoO_3$, 2.73 g $V_2O_5$, and 3.67 g $Te(OH)_6$ to 70 mL deionized water at T=80° C. with stirring for 10 minutes. Separately, 5.73 g $NH_4NbO(C_2O_4)_2$ powder (19.5 wt % Nb) was dissolved in 30 mL deionized water at T=80° C., and then added to the first solution. After stirring for 30 minutes, the solution was cooled to room temperature and the pH was adjusted to 2.37 using aqueous 28 wt % $NH_3$ followed by transfer of equal parts of the reaction solution to four 45 mL PTFE lined autoclaves. Nitrogen was bubbled through each autoclave for 5 minutes before sealing, and then the autoclaves were placed in an oven heated to T=175° C. for 44 hours. Upon cooling, the resulting product was washed and centrifuged two times and dried overnight at 80° C. to produce a powder. The dried powder was then annealed at 600° C. for two hours under a flow of Ar. The resulting oxide has a nominal composition $Mo_{1.0}V_{0.3}Nb_{0.12}Te_{0.16}$.

Example 1

A MoVNbTe oxide was synthesized by adding 10.13 g $MoO_3$, 1.92 g $V_2O_5$, and 1.79 g $TeO_2$ to 68 mL deionized water at T=80° C. with stirring for 10 minutes. Next, 4.05 g $NH_4NbO(C_2O_4)_2$ powder (19.5 wt % Nb) was added directly to the Mo—V—Te solution with stirring for an additional 30 minutes. The solution was cooled to room temperature and the pH was adjusted to 2.49 using aqueous 28 wt % $NH_3$ followed by transfer of the solution to a 125 mL PTFE lined autoclave. Nitrogen was bubbled through the autoclave for 5 minutes before sealing, and then the autoclave was placed in an oven heated to T=175° C. for 39 hours. Upon cooling, the resulting product was washed and centrifuged two times and dried overnight at 80° C. to produce a powder. 1.5 g of the powder was then pressed into a dense pellet using a cold press and a pressure of 25,000 psi, followed by annealing at 600° C. for two hours under a flow of Ar. The resulting oxide has a nominal composition $Mo_{1.0}V_{0.3}Nb_{0.12}Te_{0.16}$.

Example 2

A MoVNbTe oxide was synthesized by adding 3.62 g $MoO_3$, 0.685 g $V_2O_5$, and 0.638 g $TeO_2$ to 22 mL deionized water at T=80° C. with stirring for 10 minutes. Next, 1.48 g $NH_4NbO(C_2O_4)_2$ powder (19.5 wt % Nb) was added directly to the Mo—V—Te solution with stirring for an additional 30 minutes. The solution was cooled to room temperature and the pH was adjusted to 2.77 using aqueous 28 wt % $NH_3$ followed by transfer of the solution to a 125 mL PTFE lined autoclave. Nitrogen was bubbled through the autoclave for 5 minutes before sealing, and then the autoclave was placed in an oven heated to T=175° C. for 41 hours. Upon cooling, the resulting product was washed and centrifuged two times and dried overnight at 80° C. to produce a powder. 1.5 g of the powder was then pressed into a dense pellet using a cold press and a pressure of 25,000 psi, followed by annealing at 600° C. for four hours under a flow of Ar. The resulting oxide has a nominal composition $Mo_{1.0}V_{0.3}Nb_{0.12}Te_{0.16}$.

Example 3

A MoVNbTe oxide was synthesized by adding 10.08 g $MoO_3$, 1.91 g $V_2O_5$, and 2.57 g $Te(OH)_6$ to 50 mL deionized water at T=80° C. with stirring for 10 minutes. Separately, 4.01 g $NH_4NbO(C_2O_4)_2$ was dissolved in 20 mL deionized water at T=80° C., and then added to the first solution. After stirring for 30 minutes, the solution was cooled to room temperature and the pH was adjusted to 2.35 using aqueous 28 wt % $NH_3$ followed by transfer of the solution to a 125 mL PTFE lined autoclave. Nitrogen was bubbled through the autoclave for 5 minutes before sealing, and then the autoclave was placed in an oven heated to T=190° C. for 43 hours. Upon cooling, the resulting product was washed and centrifuged two times and dried overnight at 80° C. to produce a powder. 1.5 g of the powder was then pressed into a dense pellet using a cold press and a pressure of 25,000 psi, followed by annealing at 600° C. for two hours under a flow of Ar. The annealed pellet was then crushed with a mortar and pestle, pressed into a dense pellet using a cold press and a pressure of 25,000 psi, followed by annealing a second time at 600° C. for two hours under a flow of Ar. The resulting oxide has a nominal composition $Mo_{1.0}V_{0.3}Nb_{0.12}Te_{0.16}$.

Example 4

The inventive annealed pellet prepared in Examples 2 and 3 were ground and then characterized by x-ray powder diffraction using standard x-ray powder diffraction techniques. The x-ray diffraction pattern for Example 3 is shown in FIG. 1 in comparison to the theoretical pattern for an M1-type structure. The pattern for both annealed pellet comprised the peaks in Table A:

TABLE A

| $2\Theta$ (°) ± 0.1 |
| --- |
| 6.6 |
| 7.8 |
| 9.0 |
| 22.2 |
| 25.3 |
| 26.2 |
| 27.2 |
| 29.1 |
| 30.4 |
| 45.1 |

The catalyst prepared in Example 2 exhibited 83% crystallinity of the M1 phase and the catalyst prepared in Example 3 exhibited 90% crystallinity of the M1 phase.

Example 5

Figure 2A:
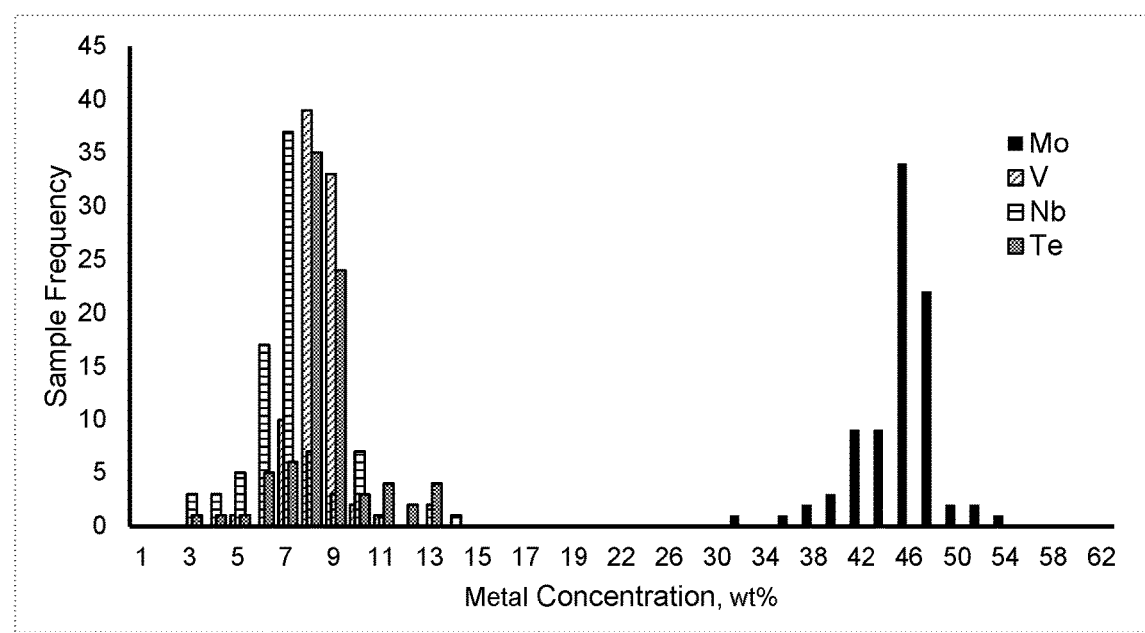
FIGS. 2A, 2B and 2C show the semi-quantitative elemental analyses of Mo, V, Nb, and Te in two inventive annealed pellets and a comparative sample (annealed powder).
Figure 2B:
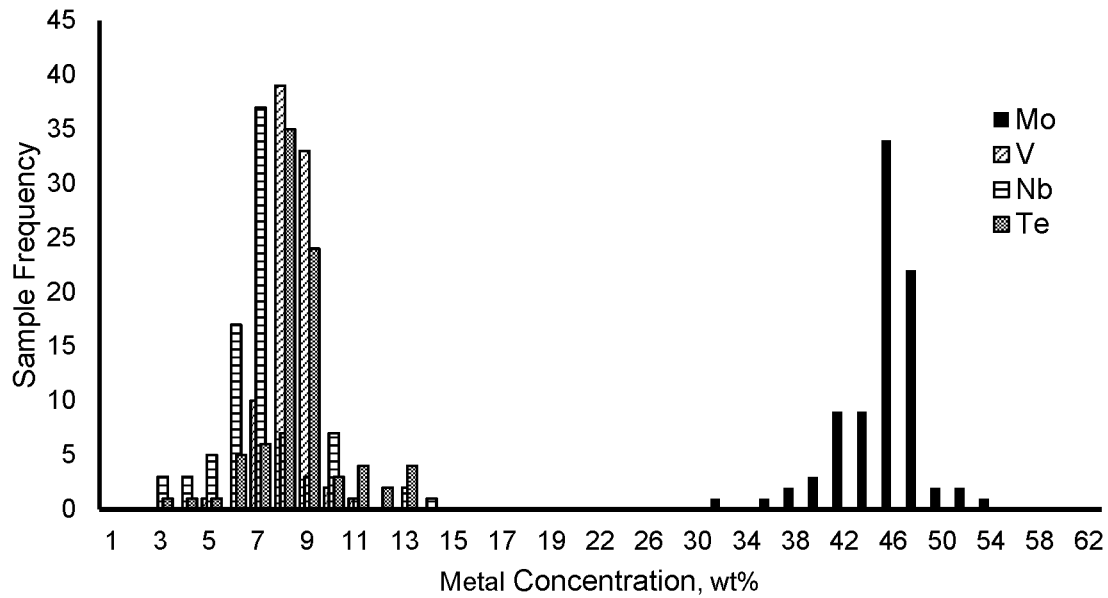
Figure 2C:
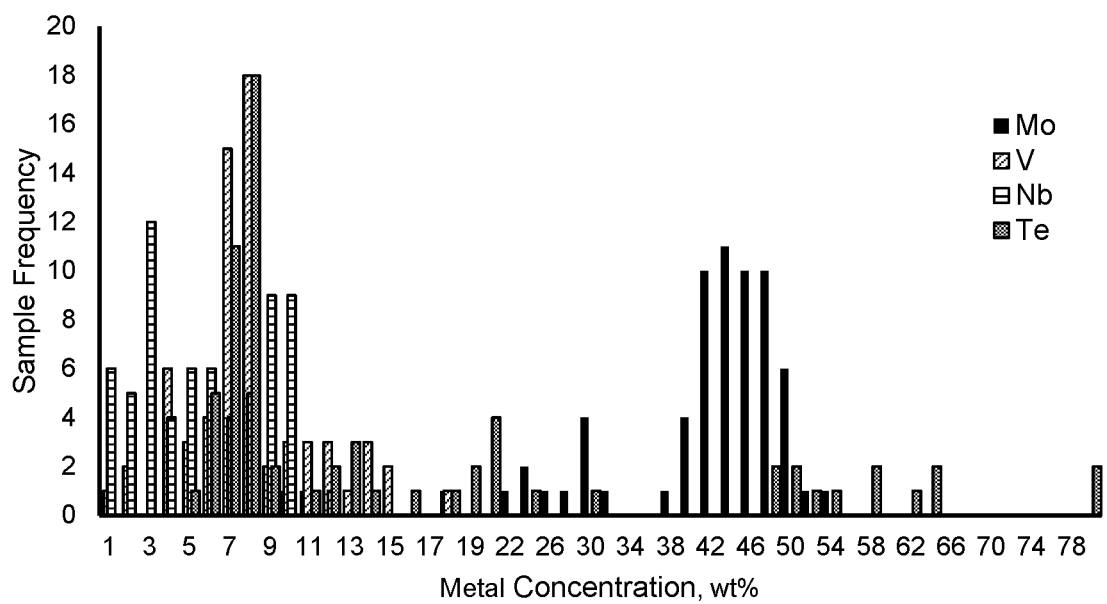

The annealed pellets prepared in inventive Examples 2 and 3 and the sample prepared in the Comparative Example were characterized using scanning electron microscopy (SEM) and energy-dispersive X-ray spectroscopy (EDS). EDS scans were collected at between 50-100 points centered on different spots of the catalyst, and the local wt % of Mo, V, Nb, and Te was quantified at each spot. The results were compiled into histograms in FIGS. 2A-2C. The SEM-EDS results show that better distribution of Mo, V, Nb, and Te in the inventive annealed pellets than in the annealed powder of the Comparative Example. In the semi-quantitative elemental analysis results shown in FIGS. 2A (Example 2) and 2B (Example 3), the inventive annealed pellets shows near Gaussian distribution of elements, while the annealed powder of the Comparative Example has wide distribution of elements (FIG. 2C). Quantitatively, the standard deviation in molybdenum wt % decreased from $\sigma_{Mo}$=9.5 wt % to $\sigma$<3.2 wt %. Similarly, the standard deviation in other elements decreased from $\sigma_V$=3.3 wt % to $\sigma_V$<0.9 wt %, $\sigma_{Nb}$=3.1 wt % to $\sigma_{Nb}$<2 wt %, and $\sigma_{Te}$=21.0 wt % to $\sigma_{Te}$<3.2 wt %.

Example 6

Inventive annealed pellets prepared as in Examples 1-3 and the Comparative Example were tested in a fixed bed flow reactor for the oxidative dehydrogenation of ethane at a temperature ranging from 300-450° C., a pressure of 15 psig, a GHSV (gas hourly space velocity) of 2000 $cm^3 \ast g_{cat}^{-1} \ast h^{-1}$ and a gas composition ratio of 1.6:1:5 to 2:1:5 ethane/$O_2$/$N_2$ using 1 g of each catalyst.

Figure 3:
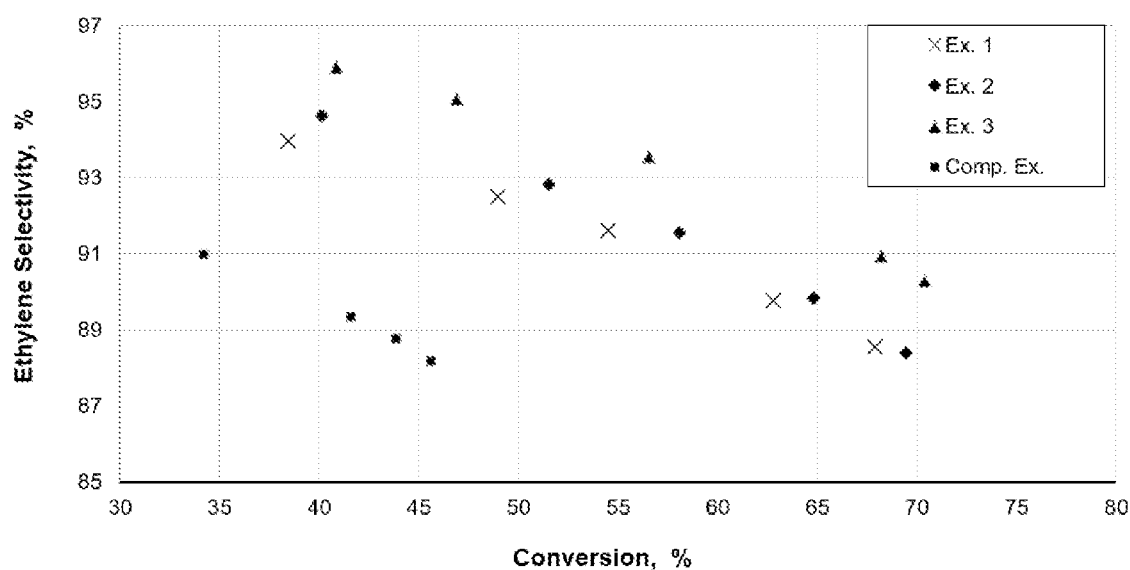
FIG. 3 shows a plot of the selectivity for the $C_2$ conversion of three inventive samples and a comparative sample, all prepared using oxide precursors and hydrothermal treatment, but with different annealing approaches.

FIG. 3 shows that the $C_2$ selectivity for the inventive annealed pellet sample is superior to that of the comparative sample made without the inventive compression step.

Specific Embodiments

While the following is described in conjunction with specific embodiments, it will be understood that this description is intended to illustrate and not limit the scope of the preceding description and the appended claims.

A first embodiment of the invention is a method for preparing a mixed-metal oxide catalyst, the method comprising (a) preparing a catalyst precursor comprising molybdenum, vanadium, at least one of niobium or tantalum, and at least one of tellurium or antimony; (b) pressing the catalyst precursor into a dense pellet using a pressure of greater than about 5,000 psi; (c) annealing the dense pellet at a temperature of from about 525° C. to about 700° C. in a non-oxidative environment for a period of from about 0.5 hours to about 24 hours to form the mixed-metal oxide catalyst; and (d) optionally grinding the mixed-metal oxide catalyst into a fine powder and repeating steps (b) and (c). An embodiment of the invention is one, any or all of prior embodiments in this paragraph up through the first embodiment in this paragraph, wherein the mixed-metal oxide catalyst has the formula $MoV_xY_yZ_zO_n$ wherein; Y=Nb, Ta, or a combination thereof Z=Te, Sb, or a combination thereof x=0.1 to 0.4, y=0.05 to 0.3, z=0.05 to 0.3, and n takes a value that satisfies the bond valency of the mixed-metal oxide catalyst; the catalyst further characterized by an x-ray powder diffraction pattern comprising peaks at the diffraction angles 2Θ (°)±0.1 of 6.6, 7.8, 9.0, 22.2, 25.3, 26.2, 27.2, 29.1, 30.4, and 45.1. An embodiment of the invention is one, any or all of prior embodiments in this paragraph up through the first embodiment in this paragraph, wherein the catalyst precursor in step (a) was produced by preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C.; optionally adjusting the pH of the slurry from about 2 to about 4; and drying the slurry to form the catalyst precursor; wherein the compounds are metallic elements, salts, acids, oxides, hydroxides, oxyhalides or mixtures thereof. An embodiment of the invention is one, any or all of prior embodiments in this paragraph up through the first embodiment in this paragraph, wherein at least one of the compounds is an oxide. An embodiment of the invention is one, any or all of prior embodiments in this paragraph up through the first embodiment in this paragraph, wherein the slurry is produced by preparing a first solution comprising a molybdenum compound, a vanadium compound, and at least one of a tellurium compound and an antimony compound; preparing a second solution at least one of a niobium compound and a tantalum compound, and admixing the first solution and the second solution. An embodiment of the invention is one, any or all of prior embodiments in this paragraph up through the first embodiment in this paragraph, wherein the catalyst precursor in step (a) was produced by preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C.; optionally adjusting the pH of the slurry from about 2 to about 4; and hydrothermally treating the catalyst precursor at a temperature from about 150° C. to about 250° C. for about 10 to about 100 hours; wherein the compounds are metallic elements, salts, acids, oxides, hydroxides, oxyhalides or mixtures thereof. An embodiment of the invention is one, any or all of prior embodiments in this paragraph up through the first embodiment in this paragraph, wherein at least one of the compounds is an oxide. An embodiment of the invention is one, any or all of prior embodiments in this paragraph up through the first embodiment in this paragraph, wherein the slurry is produced by preparing a first solution comprising a molybdenum compound, a vanadium compound, and at least one of a tellurium compound and an antimony compound; preparing a second solution at least one of a niobium compound and a tantalum compound, and admixing the first solution and the second solution. An embodiment of the invention is one, any or all of prior embodiments in this paragraph up through the first embodiment in this paragraph, wherein the dense pellet is produced by using a pressure of greater than about 15,000 psi. An embodiment of the invention is one, any or all of prior embodiments in this paragraph up through the first embodiment in this paragraph, wherein after step (b), the dense pellet is calcined in an oxidative environment, at a temperature between about 250° C. to about 350° C., before annealing step (c) is carried out. An embodiment of the invention is one, any or all of prior embodiments in this paragraph up through the first embodiment in this paragraph wherein the mixed-metal oxide catalyst has the formula $MoV_xNb_yTe_zO_n$ wherein x=0.2 to 0.35, y=0.1 to 0.15, z=0.15 to 0.25; and wherein n takes a value that satisfies the bond valency of the mixed-metal oxide catalyst. An embodiment of the invention is one, any or all of prior embodiments in this paragraph up through the first embodiment in this paragraph wherein the crystalline portion of the mixed-metal oxide catalyst is greater than about 80%.

A second embodiment of the invention is a mixed-metal oxide catalyst for the oxidative dehydrogenation of ethane to ethylene, the catalyst prepared by the method comprising (a) preparing a catalyst precursor comprising molybdenum, vanadium, at least one of niobium or tantalum, and at least one of tellurium or antimony; (b) pressing the catalyst precursor into a dense pellet using a pressure of greater than about 5,000 psi; (c) annealing the dense pellet at a temperature of from about 525° C. to about 700° C. in a non-oxidative environment for a period of from about 0.5 hours to about 24 hours to form the mixed-metal oxide catalyst; and (d) optionally grinding the mixed-metal oxide catalyst into a fine powder and repeating steps (b) and (c). An embodiment of the invention is one, any or all of prior embodiments in this paragraph up through the second embodiment in this paragraph, wherein the mixed-metal oxide catalyst has the formula $MoV_xY_yZ_zO_n$ wherein; Y=Nb, Ta, or a combination thereof Z=Te, Sb, or a combination thereof x=0.1 to 0.4, y=0.05 to 0.3, z=0.05 to 0.3, and n takes a value that satisfies the bond valency of the mixed-metal oxide catalyst; the catalyst further characterized by an x-ray powder diffraction pattern comprising peaks at the diffraction angles 2Θ (°)±0.1 of 6.6, 7.8, 9.0, 22.2, 25.3, 26.2, 27.2, 29.1, 30.4, and 45.1. An embodiment of the invention is one, any or all of prior embodiments in this paragraph up through the second embodiment in this paragraph, wherein the catalyst precursor in step (a) was produced by preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C.; optionally adjusting the pH of the slurry from about 2 to about 4; and drying the slurry to form the catalyst precursor; wherein the compounds are metallic elements, salts, acids, oxides, hydroxides, oxyhalides or mixtures thereof. An embodiment of the invention is one, any or all of prior embodiments in this paragraph up through the second embodiment in this paragraph, wherein the catalyst precursor in step (a) was produced by preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C.; optionally adjusting the pH of the slurry from about 2 to about 4; and hydrothermally treating the catalyst precursor at a temperature from about 150° C. to about 250° C. for about 10 to about 100 hours; wherein the compounds are metallic elements, salts, acids, oxides, hydroxides, oxyhalides or mixtures thereof.

A third embodiment of the invention is a method for the oxidative dehydrogenation of ethane to ethylene in the presence of a mixed-metal oxide catalyst, the catalyst prepared by the method comprising (a) preparing a catalyst precursor comprising molybdenum, vanadium, at least one of niobium or tantalum, and at least one of tellurium or antimony; (b) pressing the catalyst precursor into a dense pellet using a pressure of greater than about 5,000 psi; (c) annealing the dense pellet at a temperature of from about 525° C. to about 700° C. in a non-oxidative environment for a period of from about 0.5 hours to about 24 hours to form the mixed-metal oxide catalyst; and (d) optionally grinding the mixed-metal oxide catalyst into a fine powder and repeating steps (b) and (c). An embodiment of the invention is one, any or all of prior embodiments in this paragraph up through the third embodiment in this paragraph, wherein the mixed-metal oxide catalyst has the formula $MoV_xY_yZ_zO_n$ wherein; Y=Nb, Ta, or a combination thereof Z=Te, Sb, or a combination thereof x=0.1 to 0.4, y=0.05 to 0.3, z=0.05 to 0.3, and n takes a value that satisfies the bond valency of the mixed-metal oxide catalyst; the catalyst further characterized by an x-ray powder diffraction pattern comprising peaks at the diffraction angles 2Θ (°)±0.1 of 6.6, 7.8, 9.0, 22.2, 25.3, 26.2, 27.2, 29.1, 30.4, and 45.1. An embodiment of the invention is one, any or all of prior embodiments in this paragraph up through the third embodiment in this paragraph, wherein the catalyst precursor in step (a) was produced by preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C.; optionally adjusting the pH of the slurry from about 2 to about 4; and drying the slurry to form the catalyst precursor; wherein the compounds are metallic elements, salts, acids, oxides, hydroxides, oxyhalides or mixtures thereof. An embodiment of the invention is one, any or all of prior embodiments in this paragraph up through the third embodiment in this paragraph, wherein the catalyst precursor in step (a) was produced by preparing a slurry comprising a molybdenum compound, a vanadium compound, at least one of a niobium compound and a tantalum compound, and at least one of a tellurium compound and an antimony compound; optionally heating the slurry at a temperature of from about 60° C. to about 90° C.; optionally adjusting the pH of the slurry from about 2 to about 4; and hydrothermally treating the catalyst precursor at a temperature from about 150° C. to about 250° C. for about 10 to about 100 hours; wherein the compounds are metallic elements, salts, acids, oxides, hydroxides, oxyhalides or mixtures thereof.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

We claim:

1. A mixed-metal oxide catalyst for the oxidative dehydrogenation of ethane to ethylene, the catalyst prepared by the method comprising:
   (a) preparing a catalyst precursor comprising molybdenum, vanadium, at least one of niobium or tantalum, and at least one of tellurium or antimony;
   (b) pressing the catalyst precursor into a dense pellet using a pressure of greater than about 5,000 psi;
   (c) annealing the dense pellet at a temperature of from about 525° C. to about 700° C. in a non-oxidative environment for a period of from about 0.5 hours to about 24 hours to form the mixed-metal oxide catalyst; and
   (d) optionally grinding the mixed-metal oxide catalyst into a fine powder and repeating steps (b) and (c),
   wherein after annealing of the dense pellet in step (c), the mixed-metal oxide catalyst is characterized by a local distribution of elements comprising of a standard deviation in molybdenum decreasing in a range of $\sigma_{Mo}$=9.5 wt % to $\sigma_{Mo}$<3.2 wt %, and a standard deviation in vanadium decreasing in a range of $\sigma_v$=3.3 wt % to a $\sigma_v$<0.9 wt %.

2. The mixed-metal oxide catalyst of claim 1, wherein the mixed-metal oxide catalyst has the formula

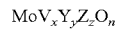

wherein;
   Y=Nb, Ta, or a combination thereof
   Z=Te, Sb, or a combination thereof
   x=0.1 to 0.4,
   y=0.05 to 0.3,
   z=0.05 to 0.3, and
   n takes a value that satisfies the bond valency of the mixed-metal oxide catalyst;
   the catalyst further characterized by an x-ray powder diffraction pattern comprising peaks at the diffraction angles 2Θ (°)±0.1 of 6.6, 7.8, 9.0, 22.2, 25.3, 26.2, 27.2, 29.1, 30.4, and 45.1.

3. The mixed-metal oxide catalyst of claim 1, wherein the catalyst precursor in step (a) was produced by:
   preparing a slurry comprising a molybdenum compound, a vanadium compound, at least one of a niobium compound and a tantalum compound, and at least one of a tellurium compound and an antimony compound;

optionally heating the slurry at a temperature of from about 60° C. to about 90° C.;

optionally adjusting the pH of the slurry from about 2 to about 4; and hydrothermally treating the catalyst precursor at a temperature from about 150° C. to about 250° C. for about 10 to about 100 hours;

wherein the compounds are metallic elements, salts, acids, oxides, hydroxides, oxyhalides or mixtures thereof.

4. The method of claim 3, wherein at least one of the compounds is an oxide.

5. The method of claim 3, wherein the slurry is produced by:

preparing a first solution comprising a molybdenum compound, a vanadium compound, and at least one of a tellurium compound and an antimony compound;

preparing a second solution at least one of a niobium compound and a tantalum compound, and admixing the first solution and the second solution.

6. The method of claim 1, wherein the dense pellet is produced by using a pressure of greater than about 15,000 psi.

7. The method of claim 1, wherein after step (b), the dense pellet is calcined in an oxidative environment, at a temperature between about 250° C. to about 350° C., before annealing step (c) is carried out.

8. The mixed-metal oxide catalyst of claim 2 has the formula $$MoV_xNb_yTe_zO_n$$

wherein x=0.2 to 0.35, y=0.1 to 0.15, z=0.15 to 0.25; and wherein n takes a value that satisfies the bond valency of the mixed-metal oxide catalyst.

9. The mixed metal oxide catalyst of claim 2 wherein the crystalline portion of the mixed-metal oxide catalyst is greater than about 80%.

10. A method of oxidative dehydrogenating ethane to ethylene in the presence of a mixed-metal oxide catalyst comprising contacting a gas composition containing ethane with the mixed metal oxide catalyst in the temperature range of 300-450° C., a pressure of 15 psig, a gas hourly space velocity of 2000 cm³/h per gram of the mixed metal oxide catalyst, wherein the gas composition having a ratio of ethane:$O_2$:$N_2$ in a range from 1.6:1:5 to 2:1:5; wherein the mixed metal oxide catalyst prepared by the method comprising:

a. preparing a catalyst precursor comprising molybdenum, vanadium, at least one of niobium or tantalum, and at least one of tellurium or antimony;

b. pressing the catalyst precursor into a dense pellet using a pressure of greater than about 5,000 psi;

c. annealing the dense pellet at a temperature of from about 525° C. to about 700° C. in a non-oxidative environment for a period of from about 0.5 hours to about 24 hours to form the mixed-metal oxide catalyst; and d. optionally grinding the mixed-metal oxide catalyst into a fine powder and repeating steps (b) and (c), wherein after annealing of the dense pellet in step (c), the mixed-metal oxide catalyst is characterized by a local distribution of elements comprising of a standard deviation in molybdenum decreasing in a range of $\sigma_{Mo}$=9.5 wt % to $\sigma$<3.2 wt %, and a standard deviation in vanadium decreasing in a range of $\sigma_v$=3.3 wt % to $\sigma_v$<0.9 wt %.

11. The method of claim 10, wherein the mixed-metal oxide catalyst has the formula $$MoV_xY_yZ_zO_n$$

wherein;

Y=Nb, Ta, or a combination thereof

Z=Te, Sb, or a combination thereof x=0.1 to 0.4, y=0.05 to 0.3, z=0.05 to 0.3, and n takes a value that satisfies the bond valency of the mixed-metal oxide catalyst;

the catalyst further characterized by an x-ray powder diffraction pattern comprising peaks at the diffraction angles 2θ (°)±0.1 of 6.6, 7.8, 9.0, 22.2, 25.3, 26.2, 27.2, 29.1, 30.4, and 45.1.

12. The method of claim 10, wherein the catalyst precursor in step (a) was produced by:

preparing a slurry comprising a molybdenum compound, a vanadium compound, at least one of a niobium compound and a tantalum compound, and at least one of a tellurium compound and an antimony compound;

optionally heating the slurry at a temperature of from about 60° C. to about 90° C.;

optionally adjusting the pH of the slurry from about 2 to about 4; and drying the slurry to form the catalyst precursor;

wherein the compounds are metallic elements, salts, acids, oxides, hydroxides, oxyhalides or mixtures thereof.

13. The method of claim 10, wherein the catalyst precursor in step (a) was produced by:

preparing a slurry comprising a molybdenum compound, a vanadium compound, at least one of a niobium compound and a tantalum compound, and at least one of a tellurium compound and an antimony compound;

optionally heating the slurry at a temperature of from about 60° C. to about 90° C.;

optionally adjusting the pH of the slurry from about 2 to about 4; and hydrothermally treating the catalyst precursor at a temperature from about 150° C. to about 250° C. for about 10 to about 100 hours;

wherein the compounds are metallic elements, salts, acids, oxides, hydroxides, oxyhalides or mixtures thereof.

\* \* \* \* \*